United States Patent [19]
Mavinkurve

[11] Patent Number: 5,275,591
[45] Date of Patent: Jan. 4, 1994

[54] FLUID BARRIER SEAL FOR SANITARY NAPKIN HAVING UNDERGARMENT PROTECTING FLAPS

[75] Inventor: Pramod S. Mavinkurve, Kendall Park, N.J.

[73] Assignee: McNeil-PPC, Inc., Milltown, N.J.

[21] Appl. No.: 818,494

[22] Filed: Jan. 8, 1992

Related U.S. Application Data

[63] Continuation of Ser. No. 640,713, Jan. 14, 1991, abandoned, which is a continuation of Ser. No. 467,322, Jan. 18, 1990, abandoned, which is a continuation of Ser. No. 78,139, Jul. 27, 1987, abandoned.

[51] Int. Cl.⁵ .............................................. A61F 13/15
[52] U.S. Cl. ................... 604/387; 604/385.1; 604/378; 604/389
[58] Field of Search ............ 604/376, 366, 370, 385.1, 604/387, 386, 390, 385.2

[56] References Cited

U.S. PATENT DOCUMENTS

| | | | |
|---|---|---|---|
| 4,285,343 | 8/1981 | McNair | 604/387 |
| 4,321,924 | 3/1982 | Ahr | 604/378 |
| 4,526,825 | 7/1985 | Whitehead | 604/378 |
| 4,579,556 | 4/1986 | McFarland | 604/385.2 |
| 4,584,876 | 5/1986 | Vantilburg | 604/385.1 |
| 4,608,047 | 8/1986 | Mattingly | 604/387 |
| 4,650,481 | 3/1987 | O'Connor et al. | 604/370 |
| 4,687,478 | 8/1987 | Van Tilburg | 604/387 |
| 4,752,349 | 6/1988 | Gebel | 156/267 |
| 4,755,413 | 7/1988 | Morris | 428/138 |
| 4,759,754 | 7/1988 | Korpman | 604/387 |
| 4,911,701 | 3/1990 | Mavinkurve | 604/385.2 |
| 4,917,697 | 4/1990 | Osborn et al. | 604/387 |
| 4,936,839 | 6/1990 | Molee et al. | 604/378 |
| 4,940,462 | 7/1990 | Salerno | 604/387 |
| 5,037,418 | 8/1991 | Kons et al. | 604/387 |
| 5,133,704 | 7/1992 | Wheeler | 604/387 |
| 5,133,705 | 7/1992 | Nakanishi | 604/387 |
| 5,154,715 | 10/1992 | Van Iten | 604/387 |

Primary Examiner—C. Fred Rosenbaum
Assistant Examiner—Mark O. Polutta

[57] ABSTRACT

A sanitary napkin having flaps extending laterally from each of the longitudinal sides of its central absorbent is provided with body fluid sealing means disposed between the absorbent element and at least one of the flaps for restricting the transmission of body fluid from the absorbent element into the flap. The napkin construction creates a plurality of absorption compartments that can minimize staining of undergarments by body fluid.

23 Claims, 3 Drawing Sheets

FLUID BARRIER SEAL FOR SANITARY NAPKIN HAVING UNDERGARMENT PROTECTING FLAPS

This is a continuation of application Ser. No. 640,713, filed Jan. 14, 1991, which was a continuation of U.S. Ser. No. 467,322 filed Jan. 18, 1990 abandoned, which was in turn a continuation of U.S. Ser. No. 078,139 filed Jul. 27, 1987.

CROSS REFERENCE TO RELATED APPLICATION

This application is related to copending and commonly assigned application Ser. No. 07/090,174, filed Aug. 27, 1987, in the names of Ken Molee and Ken Wilson, having attorney docket number (PPC-296) entitled "Winged Napkin having Cross-Channeling" now U.S. Pat. No. 4,773,905.

FIELD OF THE INVENTION

This invention relates to protective, absorbent liners for undergarments, and more particularly, to improved sanitary protection for napkins having undergarment protecting flaps.

BACKGROUND OF THE INVENTION

Sanitary napkins have customarily included a central absorbent element having a body facing side, a garment facing side, longitudinally extending sides and transverse ends. In the past, these products sometimes failed to provide proper protection because the edges of the crotch of the panty, to which these products are adhered, tended to enfold onto the body facing side of the napkin. This condition can cause the panty to be stained with body fluid, either emanating from the napkin or exuding from the body of the wearer.

In order to overcome this deficiency, several of the more recent napkin designs have included flaps extending along the longitudinal sides of the absorbent element. Mattingly, U.S. Pat. No. 4,608,047, for example, is directed to such a sanitary napkin having flaps extending from a central absorbent. This product is adhesively attached to an inner crotch portion of a users' undergarment and its side flaps are then folded onto an outer surface of the crotch portion to protect the garment. McNair, U.S. Pat. No. 4,285,343, is also directed to a napkin having flaps for folding over the outer surface of the wearer's undergarment. Both of these patents provide for embodiments that include absorbent pads in their flaps, thereby inviting the transmission of body fluid from the central absorbent element into the flaps.

Von Tilberg, U.S. Pat. No. 4,589,876, is directed to a sanitary napkin that includes a central absorbent pad and two flaps extending laterally from the pad. This napkin design preferentially bends at a line of juncture between each flap and the longitudinal edges of the central absorbent pad. The flaps of this napkin comprise a liquid pervious top sheet, a liquid impervious back sheet and an absorbent core interposed between the top sheet and back sheet. Additionally, each flap has a flexible axis located in the body of the flap which allows the flap to be folded onto itself to form a gasket-like seal between the body of the user and the flaps along the flexible axis in the body of the flaps. This patent requires the use of "good body contact" to provide a barrier to lateral flow of menstrual fluid from the crotch area.

It is understood that when fluid comes in contact with the pulp of the central absorbent, it is readily absorbed by a series of large capillaries in the pulp structure. This fluid travels through the molded pulp of these napkins and meets the often used bottom tissue which has very small capillaries. When fluid reaches these fine capillaries it travels at a faster rate and spreads through the tissue into the flaps. The molded pulp and the tissue consequently become one absorbent system. One major drawback of this system is that the absorbent tissue in the flaps may draw body fluid away from the central absorbent element and out of the inner crotch portion of the undergarment, creating a potential for staining the garments of the wearer.

Although not directed to napkins with flaps. some prior art products teach the use of sealing means in their central absorbent.

Whitehead, U.S. Pat. No. 4,526,825, is directed to a sanitary appliance having a fused barrier for sealing fluid run off and wicking migration. The barrier of this patent is created by fusing the fluid permeable wrap around the periphery of the central absorbent. This napkin does not provide flaps for protecting the undergarment, nor does it appreciate the value of compartmentalized absorbency.

Black, U.S. Pat. No. 4,200,103 discloses a napkin design having at least two fluid barrier seal lines extending longitudinally with the product and sealing the longitudinal edge portion of the napkin's barrier sheet to the cover portion. This napkin is not concerned with the transmission of body fluid out of the crotch portion through laterally extending flaps. This patent also does not teach absorbent material located outside the central pad area for protection against body fluid which may run off the surface of the pad and along the body.

Ahr, U.S. Pat. No. 4,321,924, and Csillag, U.S. Pat. No. 4,015,604, disclose fluid barriers within or along the perimeter of their central absorbent elements and supplemental absorbent areas outside of the central absorbent. Csillag refers to the supplemental absorbent areas as margins that provide a comfortable interface between the hydrophobic zones of the central absorbent when the product is worn. Csillag warns that the zones should not be so wide as to substantially detract from the body fluid absorbing capacity of the product as a whole, thus indicating that the zones are designed for comfort rather than absorbency. Ahr states that his border provides added protection against undergarment soiling from discharged fluids which flow across the top sheet and beyond the absorbent core. These patents, however, fail to disclose absorbent wing members that may be folded around the outer portion of an undergarment for protecting the panty against soiling. Furthermore, these designs are not concerned with the problems associated with absorbing flaps and the transmission of body fluid through the napkin and out of the inner crotch portion of the undergarment.

Accordingly, there is still a need for a winged sanitary napkin that provides a barrier for preventing fluid transfer via tissue wicking from the central absorbent element to the flaps. There is also a need for a sanitary napkin that provides for compartmentalized absorbency of its flaps as a reserve to be used in exceptional circumstances.

SUMMARY OF THE INVENTION

A sanitary napkin having side flaps is provided with body fluid sealing means disposed between the absorbent element of the napkin and at least one of the flaps of the napkin for reducing the transmission of body fluid from the absorbent element into the flap. Preferably this body fluid sealing means is disposed around the entire periphery of each of the flaps to produce an absorbent reserve within each flap. Thus, there is created three compartments consisting of a central absorbent compartment and two secondary flap compartments. The primary absorbing compartment preferably comprises all the absorbent pulp material while the secondary flap compartment preferably comprises only a light weight tissue. This compartmentalization can be achieved by placing an inner fluid barrier seal along the entire longitudinal edge of the pulp pad adjacent both flaps. As used herein, a "fluid barrier seal" refers to any sealing means which will prevent body fluid from transferring either by wicking or seeping across the seal.

The central absorbent of the preferred embodiment is the primary absorbing compartment while the flaps are preferably used only as backup compartments to absorb fluid from occasional gushing, from fluid that could have been smeared on to the body, or from leaky, misplaced napkins. The inner fluid barrier seal creates discreet compartments so that fluid absorbed by the primary absorbent does not transfer into the flap compartments.

Thus, a sanitary napkin is provided that prevents fluid transfer via tissue wicking from the central absorbent to the flaps. This invention also provides for absorbent reserve areas in the flaps of the sanitary napkin to be used in exceptional circumstances, such as those enumerated above.

It is, therefore, an object of this invention to provide a sanitary napkin having flaps that can be folded over an outer portion of the crotch of an undergarment without causing body fluid to transfer out of the crotch area.

It is another object of this invention to provide a sanitary napkin that creates absorbent reserve areas to act as backup compartments to absorb fluid that could have smeared on to the body.

It is still another object of this invention to provide a sanitary napkin that has sealed flap absorbent compartments with absorbent tissue disposed therein.

With these and other objects in view, which will become apparent to one skilled in the art as the description proceeds, this invention resides in the novel construction, combination, arrangement of parts and methods substantially as hereinafter described and more particularly defined by the attached claims.

BRIEF DESCRIPTION OF THE DRAWINGS

The accompanying drawings illustrate a complete embodiment of the invention according to the best mode for the best practical application of the principles thereof, and in which.

DETAILED DESCRIPTION OF THE INVENTION

Figure 1:
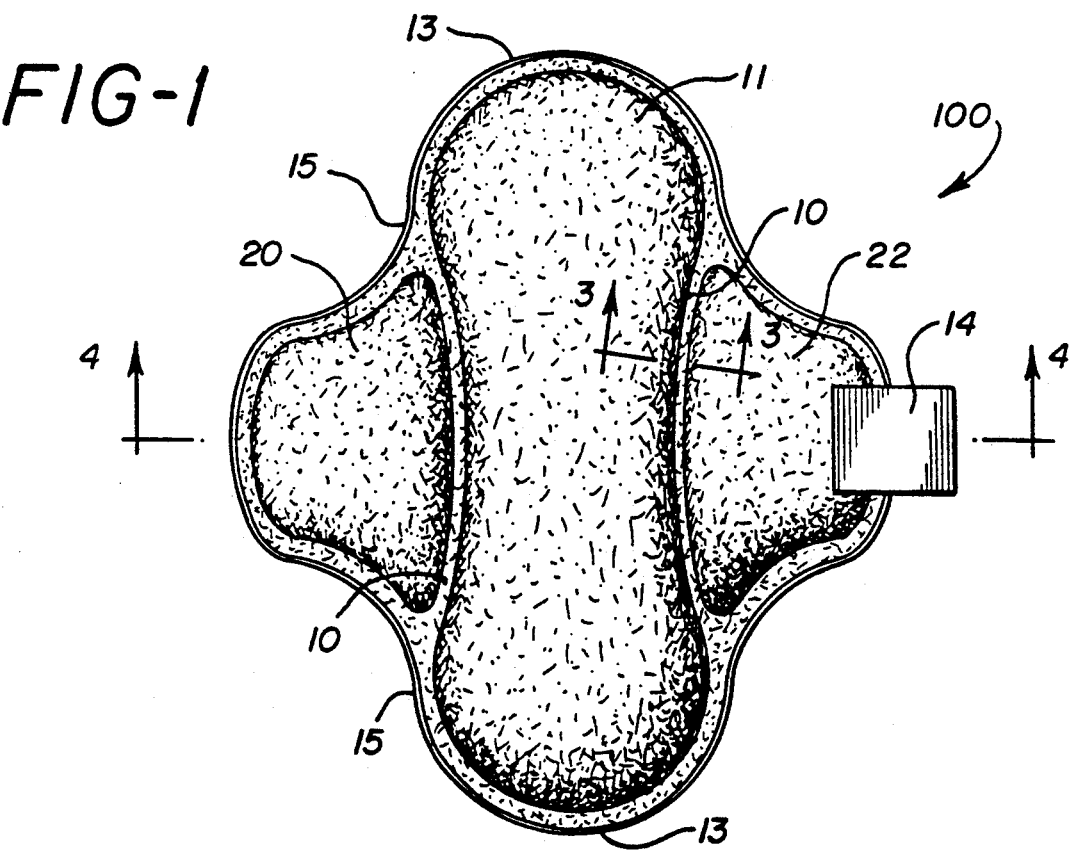
FIG. 1: is a planar view of the body facing side of a sanitary napkin embodiment of this invention illustrating the fluid barrier seal disposed between the flaps and the absorbent element of the napkin.

In accordance with the teachings of this invention, a sanitary napkin and a method for sealing the transmission of body fluid from an absorbent element of a sanitary napkin is provided. The sanitary napkin of this invention includes an absorbent element or pad and flaps extending laterally from each of the longitudinal sides of the pad. The napkin includes the improvement wherein a body fluid sealing means is disposed between the absorbent element and at least one of the flaps for reducing the transmission of body fluid from the absorbent pad into the flap. The invention also can include sealing means disposed around the entire periphery of each of the flaps, thereby creating an absorbent reserve within each of these flaps.

Also described herein is a method for sealing the transmission of body fluid from an absorbent element of a sanitary napkin having longitudinally extending sides and transverse ends and having flaps extending laterally from each of its longitudinal sides. This method includes providing an absorbent element having flaps that comprise a body fluid pervious cover, a body fluid impervious backing and absorbent material such as tissue disposed therein. This method provides for sealing against the transmission of body fluid by heat sealing the cover and/or backing, whereby at least a portion of the cover and/or backing is melted through the absorbent material to form a seal.

In an alternative method of this invention, the seal is provided by utilizing a hot melt adhesive to provide a body fluid seal between the flaps and the absorbent element for reducing, preferably preventing, the transmission of body fluid from the absorbent element across the seal and into the flaps.

Referring now to FIGS. 1-4, there is illustrated in planar and cross-sectional views a preferred sanitary napkin 100 embodying the teachings of this invention. The sanitary napkin 100 comprises an absorbent element 11 having longitudinally extending sides 15 and transverse ends 13. This napkin 100 further includes flaps 20 and 22 extending laterally from each of the longitudinal sides 15 of the absorbent element 11. In an important aspect of this invention, body fluid sealing means 10 is disposed between the absorbent element 11 and at least one of the flaps 20 or 22 for reducing the transmission of body fluid from the absorbent element 11 across such sealing means and into flap 20 or 22.

In a more preferred embodiment, the fluid sealing means 10 is disposed along the entire boundary between the absorbent element 11 and each of the flaps 20 and 22 for preventing the transmission of body fluid from the absorbent element 11 into each of the flaps. Sealing means 10 is preferably disposed around the entire periphery of the absorbent element 11, so that body fluid does not escape from the transverse ends 13 of the sanitary napkin 100. It is also expected that the flaps 20 and 22 can comprise an absorbent material, and further, that the flaps 20 and 22 comprise a sealing means around their entire periphery, thereby creating a sealed absorbent reserve within each of the flaps 20 and 22.

Figure 2:
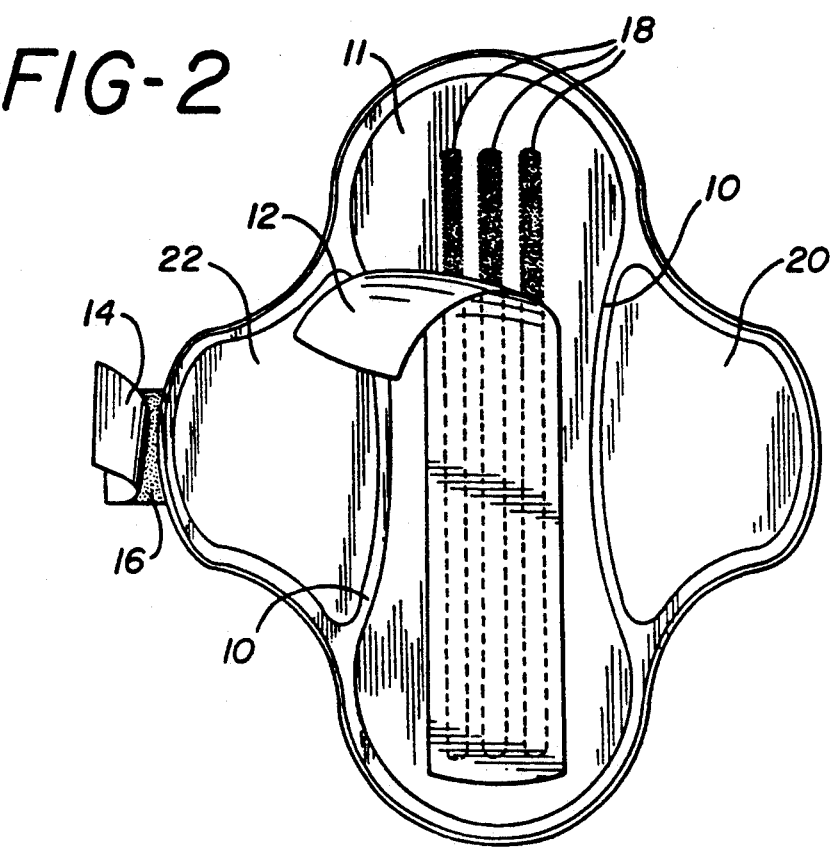
FIG. 2: is a planar view of a sanitary napkin embodiment of this invention illustrating the undergarment facing side and adhesive strips of this napkin.

The absorbent element 11 of this invention should be made of soft, comfortable material. Preferably this element 11 is cut into an "hour glass shape" as illustrated in FIGS. 1 and 2. Adequate absorbency may be built into the core of the absorbent without adding bulk by adding superabsorbent materials, now known, which have the properties of high-liquid retention, for example, cross-linked acrylate polymers. The absorbent element 11 should retain fluid well without allowing it to squeeze out and re-wet the wearer.

Generally, the absorbent element 11 should be about 4-10 inches in length, preferably about 6-9 inches. As described in FIG. 3, the absorbent element 11 comprises an absorbent core 34 which preferably is made of loosely associated absorbent hydrophilic materials such as cellulose fibers, wood pulp, regenerated cellulose or cotton fiber, and/or other materials generally known in the art. Such fibers may be chemically or physically modified and the core may include such fibers in combination with other materials, both natural and synthetic, including other fibers, foams, polymers, and the like. However, for the preferred embodiment of this invention, wood pulp is the material of choice because of its availability and inexpensive cost.

As is customary in the art, a body fluid pervious surface 32 covers the side of the napkin to be worn against the body of the user. Surface 32 can be a resilient, relatively non-absorbing, fluid pervious material. This material is provided for comfort and conformability and directs fluid to the underlying absorbent core, for example, wood pulp, which retains such fluid. This surface 32 may be any woven or non-woven material pervious to body fluid contacting its surface, and should be soft and easily permeated by body fluids. Preferably, this surface 32 should be made of a material which allows the passage of fluid without wicking it appreciably in its horizontal plane. Furthermore, it should retain little or no fluid in its structure to provide a relatively dry surface next to the skin. Generally, the fluid permeable surface 32 is a single, rectangular sheet of material having a width sufficient to cover the body-facing side of the absorbent element 11. Preferably the fluid pervious surface 32 is longer than the core 34 so as to form end tabs, which may be sealed with another pervious or impervious layer to fully enclose the core 34. The fluid pervious surface 32 is preferably made of fibers or filaments of thermoplastic hydrophobic polymers such as polyethylene or polypropylene.

Underlying the core 34 of the absorbent element 11 can be another layer of absorbent material 31 to provide additional resiliency to the product. This layer 31 may be substantially wider than the core 34 of the central absorbent 11 and may extend into the flaps 20 and 22. The absorbent layer 31 may comprise a thin, absorbent layer of material such as a tissue, fabric, or the like, made of cellulosic fibers. Because such material is provided as a safety measure and is only required to contain fluid which escapes from the side edges of absorbent core 34, it need not be very absorbent at all and, in fact, may be comprised of any capillary or cellular system including hydrophobic material such as hollow polyester fibers and heat bondable polyester/polyethylene conjugate fibers. However, the preferred material is a hydrophilic fabric comprised of cellulosic fibers such as wood pulp tissue or other suitable hydrophilic woven or nonwoven material.

The sanitary napkin 100 of this invention further includes a body fluid impervious surface 36 on the undergarment-facing side of the absorbent element 11. The impervious surface may be moisture-vapor permeable to allow passage of air and moisture vapor while substantially blocking the passage of liquids to the outer surface. The impervious surface 31 may be heat sealed or fastened by way of adhesives to the core 34 or underlying absorbent material 31. Impervious surface 34 may comprise any thin, flexible, body fluid impermeable material such as a polymeric film of, for example, polyethylene, polypropylene, or cellophane, or even a normally fluid pervious material that has been treated to be impervious such as impregnated fluid repellent paper or nonwoven fabric.

Figure 3:
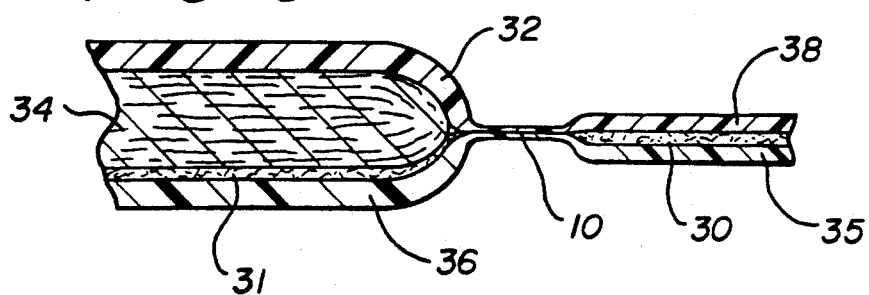
FIG. 3: is a partial, transverse, cross-sectional view of the napkin of FIG. 1, taken through line 3—3, illustrating the fluid barrier seal and preferred materials for the napkin.

An important aspect of this invention is the flaps 20 and 22 which extend laterally from each of the longitudinal sides 15 of the absorbent element 11. Although preferably not including absorbent pulp materials, these flaps 20 and 22 can include, as depicted in FIG. 3, a body fluid impervious backing 35 such as the materials described in connection with the body fluid impervious surface 36, and a body fluid pervious covers 38 such as the body fluid pervious layer 32. These flaps 20 and 22 also preferably contain absorbent tissues 30 disposed between their covers 38 and the backings 35.

Figure 4:
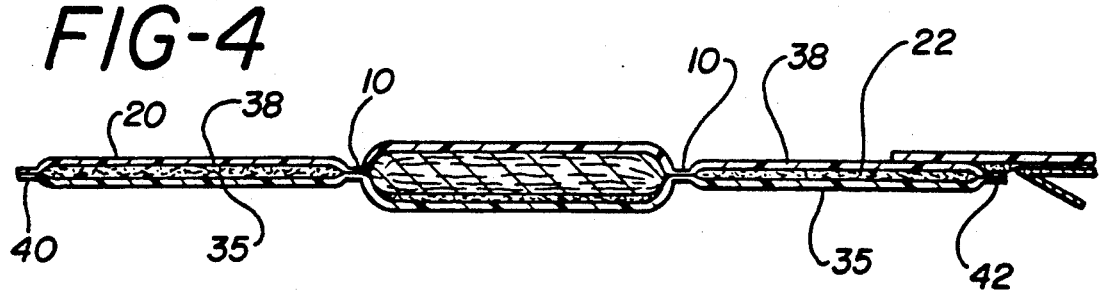
FIG. 4: is a transverse, cross-sectional view of the napkin of FIG. 4, taken through line 4—4, illustrating a preferred napkin design having sealed flaps for compartmentalized absorption.

It is preferred that the absorbent tissue 30 be an extension of the absorbent layer 31 of the central absorbent 11. This material need not be made up of hydrophilic fibers, but instead, can have sufficient capillary action to retain the small quantities of escaped liquid. Materials which are hydrophilic, for example, cellulosic fiber fabrics, may also be employed for this purpose. It should also be understood that while such materials are illustrated as extending onto the flaps 20 and 22 for the full distance from the absorbent element 11 if desired, the absorbent tissue 30 may extend only a short distance into the flaps 20 and 22. As depicted in FIG. 4, the absorbent tissue 31 can be heat sealed or adhesively sealed with the impervious backings H and body fluid pervious covers 31 to form compartmentalized absorbing areas around the edges 40 and 42 of the flaps 20 and 22.

Accordingly, as FIG. 4 depicts, a central absorbent compartment and two secondary flap compartments are created. The primary absorbent compartment can consist of all of the absorbent pulp while the secondary flap compartments preferably comprise only a light weight tissue 30, as previously discussed. Compartmentalization is achieved by an inner fluid barrier seal 10 along the entire longitudinal axis of the pulp pad adjoining both flaps. This invention therefore removes a serious drawback of prior napkins that created a single absorbent system which included the pulp and absorbent tissues. The central absorbent element 11, consisting of the bulk of the absorbent material, preferably pulp, now becomes the primary absorbing compartment and the flaps 20 and 22 are only used as backup compartments to absorb fluid that may escape from the primary absorbent. Accordingly, this invention creates discreet absorbent areas so that fluid, absorbed by the primary absorbent element 11, does not transfer directly into flap compartments by wicking through the absorbent materials.

The body fluid barrier seal 10 of this invention can consist of several material combinations. In one combination, at least a portion of the cover 38 or a portion of the backing 35 are melted through the absorbent tissues 30 and/or 31 to form body fluid sealing means 10. In this method the cover 38 can be made of apertured polyethylene or bicomponent film. The backing material 35 can also be made of heat sealable polyethylene or bicomponent film. In such a case, the cover 31, tissue 37 and backing 35 can be sealed by application of heat and pressure.

Figure 6:
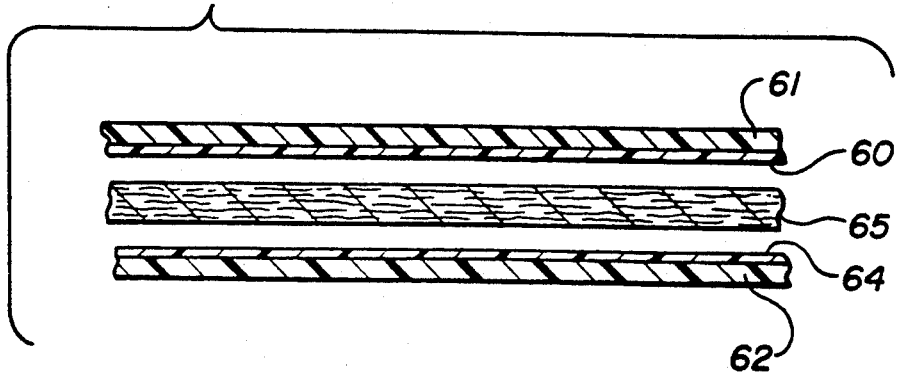
FIG. 6: is an exploded cross-sectional view of a preferred body fluid barrier seal area of this invention, prior to heat sealing.
Figure 7:
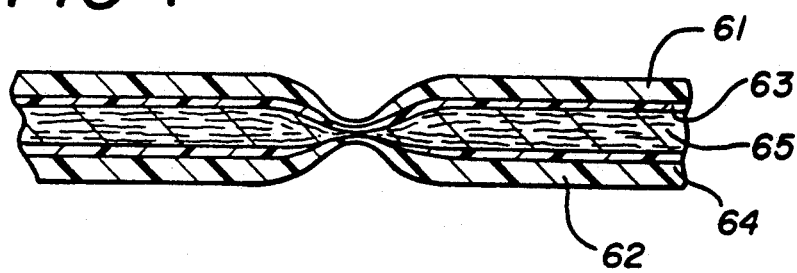
FIG. 7: is a cross-sectional view of the preferred body fluid barrier seal area of FIG. 6, after it has been heat sealed.

One preferred construction for this method includes a bicomponent cover and backing substantially as described in FIG. 6. The cover preferably comprises a coextrusion of polyethylene layer 61 and ethylene-vinyl-acetate layer 63. See Zuscik, U.S. Pat. No. 3,843,478 and Whitehead, U.S. Pat. No. 4,315,507, which are hereby incorporated by reference. Adjacent to the ethylene-vinyl-acetate layer 63 is the absorbent tissue 65, i.e. tissue 31, followed by another bicomponent barrier film. The bicomponent film corresponds with the impervious barrier layer n of the flaps 20 and 22, and preferably consists of a coextrusion of an ethylene-vinyl-acetate layer 64 next to the absorbent tissue 65 and a polyethylene layer 62 on the outside surface. Through application of heat and pressure, a fluid barrier seal, as depicted in FIG. 7, can be generated by heat flowing the ethylene-vinyl-acetate components 63 and/or 64 into the interstitial spaces of the absorbent tissue 65.

Figure 8:
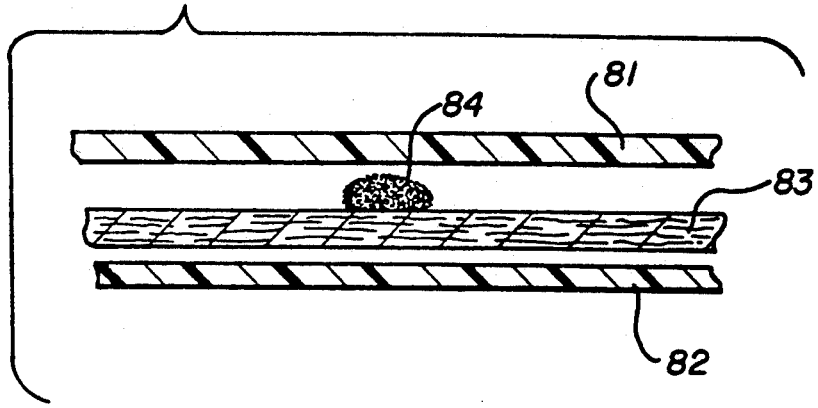
FIG. 8: is an exploded cross-sectional view of a preferred body fluid barrier seal area, illustrating the application of an adhesive.
Figure 9:
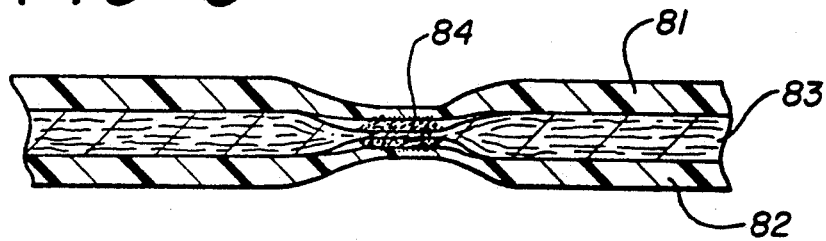
FIG. 9: is a cross-sectional view of the body fluid barrier seal area of FIG. 8 illustrating how the applied adhesive flows through the preferred absorbent tissue to join the cover and backing layers of a sanitary napkin.

In an alternative preferred construction, a hot melt adhesive 84 of FIG. 8 or other suitable adhesive substance, i.e. water based emulsions, can be placed on the preferential absorbent tissue 83. By applying heat and pressure, the preferential hot melt adhesive bonds to the cover 81 and to the backing 82, through the preferred absorbent tissue 83, substantially as described in FIG. 9, to form a fluid barrier seal 10. This construction as opposed to the heat seal design, allows a manufacturer to use a single component film as the cover 81 and backing 82.

Figure 5:
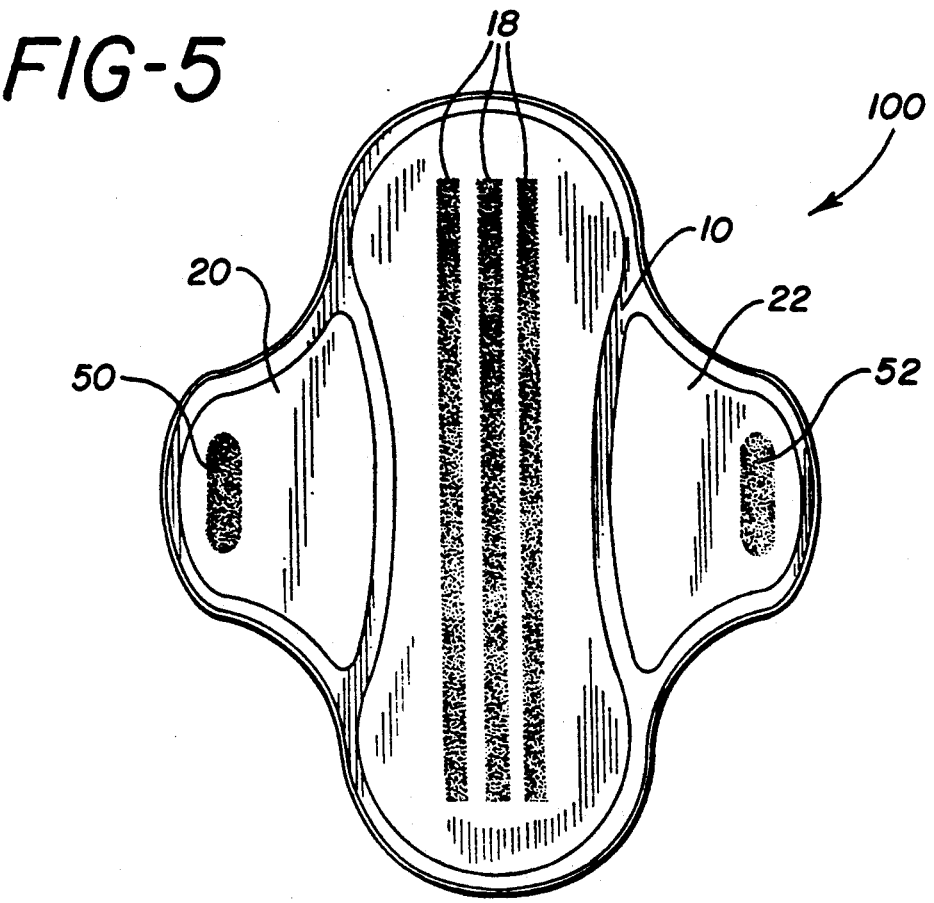
FIG. 5: is a planar view of an undergarment facing side of an alternative sanitary napkin of this invention having adhesive on both flaps.

Referring now to FIGS. 2 and 5, the attachment adhesive elements of this invention can be made of any known pressure-sensitive adhesive material. As used herein, the term "pressure-sensitive" refers to any releasable adhesive or releasable tenacious means. Adhesive compositions suitable for sanitary napkins include, for example, the water-based pressure-sensitive adhesives such as acrylate adhesives, e.g., vinyl acetate-2 ethyl hexyl acetate copolymer which is generally combined with tackifiers such as for example, ethylene amine. Alternatively, the adhesive may comprise the rapid setting thermoplastic "hot melt" adhesives. The adhesive elements may also comprise a two-sided adhesive tape. It is also anticipated that adhesives based on an elastomer selected from natural or synthetic rubbers could be used. Several adhesive placements are deemed adequate for adhering the preferred napkin 100 to an undergarment and for securing the flaps. See Mattingly, U.S. Pat. No. 4,608,047 and McNair, U.S. Pat. No. 4,285,343, which teachings are herein incorporated by reference. It will be understood that alternative shapes for these adhesives, for example, lines, squares., circles, etc., may also be employed.

FIG. 2 illustrates an embodiment having an adhesive element 16 with release strip 14 affixed to flap 22 of the napkin. The adhesive element 16 is the means for fixing the flaps 20 and 22 to the outer crotch portion of the undergarment. In this embodiment, the flaps overlap each other as they are wrapped around the outer crotch portion of the undergarment, and the adhesive element 16 is positioned to hold the napkin in place by adhering one flap to the other.

In the embodiment of FIG. 5, the napkin 100 is emplaced in the inner crotch portion of an undergarment and the flaps 20 and 22 are folded around to the outer portion of the undergarment and secured using individual adhesive means 50 and 52. This embodiment also depicts adhesive lines 18 for attaching the central absorbent to the inner crotch portion of the undergarment.

From the foregoing it can be realized that this invention provides an improved sanitary napkin with a primary absorbent which is separated from one or both of the flap compartments by a fluid barrier seal. This is a unique improvement over the current state of the art napkins having flaps and absorbent tissue disposed within their flaps. These backup flap compartments enable the napkin to absorb fluid that have smeared to the body because of napkin misplacement or occasional gushing of menstrual fluid. Although various embodiments have been illustrated, this was for the purpose of describing, but not limiting the invention. Various modifications, which will become apparent to one skilled in the art, are within the scope of this invention described in the attached claims.

What is claimed is:

1. A sanitary napkin comprising:
(a) an absorbent element having first and second longitudinally extending sides and transverse ends;
(b) first and second flaps, each of said flaps having means for wrapping portions thereof around the edges of the crotch portion of an undergarment, said first and second flaps comprising a first layer of material extending laterally from said first and second longitudinal sides of said absorbent element, respectively, each of said flaps having an edge forming an outward perimeter of said flap; and
(c) first and second fluid barrier seals for said first and second flaps, respectively, said first fluid barrier seal having a first portion disposed between said absorbent element and said first flap for reducing the transmission of body fluid from said absorbent element into said first flap and having a second portion extending along said edge of said first flap, said second fluid barrier seal having a first portion disposed between said absorbent element and said second flap for reducing the transmission of body fluid from said absorbent element into said second flap and having a second portion extending along said edge of said second flap, said first and second portions of each of said fluid barrier seals forming a compartment therebetween disposed within each of said flaps, an absorbent being disposed in each of said flap compartments to absorb fluid.

2. The sanitary napkin of claim 1 wherein each of said fluid barrier seals comprises heat sealed thermoplastic material.

3. The sanitary napkin of claim 2 wherein said heat sealed thermoplastic material comprises ethylene-vinyl-acetate.

4. The sanitary napkin of claim 3 wherein said heat sealed thermoplastic material comprises a bicomponent film of ethylene-vinyl-acetate and polyethylene.

5. The sanitary napkin of claim 4 wherein said ethylene-vinyl-acetate component of said film is sealed through a portion of said absorbent material to prevent the transmission of body fluid from said absorbent element into said flaps.

6. The sanitary napkin of claim 1 wherein each of said fluid barrier seals comprises an adhesive.

7. The sanitary napkin of claim 6 wherein said adhesive comprises a hot melt adhesive.

8. The sanitary napkin of claim 1 wherein said flap absorbent material comprises a tissue layer.

9. The sanitary napkin of claim 8 wherein said tissue layer extends beyond said flaps so as to be disposed adjacent said absorbent element.

10. The sanitary napkin of claim 8 wherein said tissue layer forms at least a portion of said absorbent element.

11. The sanitary napkin of claim 1 wherein:
(a) each of said flaps further comprising a second layer of material, said absorbent for each of said flap compartments being disposed between said first and second flap layers, said absorbent material forming interstitial spaces therewithin; and
(b) each of said fluid barrier seals formed by at least a portion of one of said layers of each of said flaps penetrating through said interstitial spaces in said absorbent material so as to bond with said other one of said flap layers.

12. The sanitary napkin of claim 11 wherein said first and second layers comprise heat sealable thermoplastic material, and wherein said fluid barrier seal is formed by melting said one of said layers through said interstitial spaces in said absorbent material.

13. The sanitary napkin of claim 1 wherein:
(a) each of said flaps further comprising a second layer of material, said absorbent for each of said flap compartments being disposed between said first and second flap layers, said absorbent material forming interstitial spaces therewithin; and
(b) each of said fluid barrier seals comprises an adhesive disposed between said first and second layers of each of said flaps, said adhesive penetrating through said interstitial spaces in said absorbent material so as to bond said flap layers together.

14. A sanitary napkin comprising
(a) an absorbent element having longitudinally extending sides and transverse ends and comprising an absorbent core, a liquid permeable cover on one side of said core, and a liquid impermeable barrier on the other side of said core,
(b) first and second flaps, each of said flaps having means for folding portions thereof around the crotch of an undergarment, each of said flaps comprising portions of said cover and said barrier that extend laterally from each of said longitudinally extending sides of said absorbent element; and
(c) a fluid barrier seal disposed between said absorbent element and each of said flaps for restricting the movement of body fluids from said absorbent element into said flaps, thereby creating compartments within each of said flaps and disposed outwardly from said seal, each of said flap compartments having means for absorbing fluid.

15. The sanitary napkin of claim 14 wherein said fluid barrier seal comprises a lamination of said cover and said barrier.

16. The sanitary napkin of claim 15 wherein said lamination extends along the entire boundary between said absorbent element and said flaps.

17. The sanitary napkin of claim 15 wherein said lamination if a heat seal.

18. The sanitary napkin of claim 17 wherein said flap compartment fluid absorbing means comprises an absorbent material disposed within each of said flap compartments between said cover and said barrier, and wherein said cover and barrier are heat sealed through said absorbent material.

19. The sanitary napkin of claim 18 wherein said seal is formed of a thermoplastic polymeric material.

20. The sanitary napkin of claim 19 wherein said polymeric material is ethylene-vinyl-acetate.

21. The sanitary napkin of claim 17 wherein at least one of said cover and said barrier comprises a heat sealable film.

22. The sanitary napkin of claim 21 wherein said film is a bicomponent film comprising a heat resistant component and a heat sealable component.

23. The sanitary napkin of claim 22 comprising a bicomponent film of polyethylene and ethylene-vinyl-acetate.

* * * * *